US00PP24222P3

(12) United States Plant Patent
Olesen

(10) Patent No.: US PP24,222 P3
(45) Date of Patent: Feb. 11, 2014

(54) MINIATURE ROSE PLANT NAMED 'POULPAH051'

(50) Latin Name: ***Rosa* hybrid**
Varietal Denomination: Poulpah051

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 62 days.

(21) Appl. No.: 13/317,257

(22) Filed: Oct. 13, 2011

(65) Prior Publication Data

US 2013/0097746 P1 Apr. 18, 2013

(51) Int. Cl.
*A01H 5/00* (2006.01)

(52) U.S. Cl.
USPC ..... Plt./117

(58) Field of Classification Search
USPC ..... Plt./117
See application file for complete search history.

(56) References Cited

PUBLICATIONS

GTITM UPOVROM Citation for 'Poulpah051' as per QZ PBR 20100217; Feb. 3, 2010.*

* cited by examiner

*Primary Examiner* — Kent L Bell

(57) ABSTRACT

A new miniature rose plant that has abundant, white flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulpah051'.

SUMMARY OF THE INVENTION

The present invention constitutes a new and distinct variety of miniature rose plant which originated from a controlled crossing between the female seed parent, an unnamed seedling, and the male pollen parent, an unnamed seedling.

The two parents were crossed during the summer of 2005 and the resulting seeds were planted in a controlled environment in Fredensborg, Denmark. The new variety, named 'Poulpah051', originated as a single seedling from the stated cross.

The new variety may be distinguished from its female seed parent primarily by flower color. The female seed parent has yellow flowers while the new variety has white flowers.

The new variety may be distinguished from its male pollen parent primarily by flower color. The male parent has yellow flowers while the new variety has white flowers.

The objective of the hybridization of this rose variety for commercial culture was to create a new and distinct variety with unique qualities, such as:

1. Uniform and abundant white flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpah051' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpah051' was selected by the inventor as a single plant from the progeny of the hybridization in 2005.

Asexual reproduction of 'Poulpah051' by cuttings and traditional budding was first done by Mogens N. Olesen in the nursery in Fredensborg, Denmark in June of 2006. This initial and other subsequent propagations conducted in controlled environments have demonstrated that the characteristics of 'Poulpah051' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'Poulpah051'.

DETAILED DESCRIPTION OF THE VARIETY

The following is a description of 'Poulpah051', as observed in its growth in glasshouses in Half Moon Bay, Calif. Observed plants are 10 weeks of age and were cultivated in 10.5 cm pots. Color references are made using The Royal Horticultural Society (London, England) Colour Chart, 2001, except where common terms of color are used.

For a comparison, several physical characteristics of the rose variety 'Poulhi012', U.S. Plant Pat. No. 14,742. are compared to 'Poulpah051' in Chart 1.

CHART 1

| | 'Poulpah051' | 'Poulhi012' |
|---|---|---|
| Petalage: | 50 | 75 to 85 |
| Flower Diameter: | 35 to 40 mm | 55 mm |
| General Tonality of Flower Color: | White Group 155A with intonations of Green-White Group 157A | Green-White Group 157C |

FLOWER AND FLOWER BUD

Blooming habit: Continuous.

Flower bud:

*Size*.—On average 25 mm in length from base of receptacle to end of bud. 19 mm in diameter.

*Bud form*.—Ovate.

*Bud color*.—As sepals unfold, petals are Yellow Group 2D and 3D.

*Sepals*.—Upper Surface: Color: Green Group 137A and 139A. Greyed-Purple Group N186C at the margins of the apex. Texture: Smooth and somewhat pubescent. Lower Surface: Color: Yellow Green Group 146B with strong intonations of Greyed-Purple Group N186C at the margins of the apex. Texture: Smooth. Shape: Apex: Cirrhose. Base: Flat at union with receptacle. Margins: Margins have moderate foliaceous appendages on three of the five sepals. Size: On average 40 mm long by 8 mm wide.

*Receptacle*.—Surface Texture: Smooth. Shape: Funnel shaped. Size: 5 mm in height by 8 mm wide. Color: Yellow Green Group 144A.

*Pedicel*.—Surface: Smooth. Length: 40 mm average length. Diameter: 3 mm. Color: Yellow-Green Group 144A. Strength: Strong.

*Borne*.—Singly.

Flower bloom:

*Fragrance*.—Light floral scent.

*Duration*.—As a pot plant, flowers last from 21 to 25 days. Petals do not fall cleanly away from plant after the duration of the flower.

*Size*.—Flower diameter is 35 to 40 mm when open. Flower depth is 35 mm.

*Form*.—General shape is similar to a hybrid tea. Double, with a high pointed center which is tightly closed.

*Shape of flower, side view*.—The upper portion is flat. The lower portion is convex.

Petalage: There are normally 50 petals, 15 of which are petaloids.

Color:

*Upon opening, petals*.—The outermost petals are Green-White Group 155C with intonations of Yellow-Green Group 145C at the margins on both upper and lower surfaces. The inner petals are White Group 155A on upper and lower surfaces.

*Upon opening, basal petal spots*.—No distinctive coloration at petal base observed.

*After opening, petals*.—The outermost and inner petals are White Group 155A on the upper and lower surfaces.

*After opening, basal petal spots*.—No distinctive coloration at petal base observed.

General tonality: On open flower White Group 155A with intonations of Green-White Group 157A. No change in the general tonality at the end of the 21$^{st}$ day.

Petals:

*Petal reflex*.—Absent.

*Petal margin*.—Entire, with a slight point at the center apex. No undulations of margin.

*Shape*.—Generally ovate. Base: Rounded. Apex: Rounded.

*Size*.—Outer petals are 40 to 45 mm in length by 20 to 22 mm wide.

*Thickness*.—Average.

*Texture*.—Smooth.

Petaloids:

*Quantity*.—Normally, there are 15 petaloids.

*Size*.—15 mm long; 7 mm wide.

*Shape*.—Irregular. Apex is rounded. Base is acute.

*Color*.—White Group 155A on upper and lower surfaces.

Reproductive organs:

*Pollen*.—None observed.

*Anthers*.—Size: 2 mm long. Color: Yellow Group 11B. Quantity: On average 55.

*Filaments*.—Color: Yellow-Green Group 145D. Length: 7 mm.

*Pistils*.—Length: 9 mm long. Quantity: About 35.

*Stigmas*.—Slightly superior relative to the length of the filaments and the height of the anthers. Color: Greyed-Yellow Group 160D.

*Styles*.—Yellow-Green Group 145D.

*Seed formation*.—Not observed.

PLANT

Plant growth: Compact and upright. 10.5 cm pot plant on its own roots, the average height of the plant itself is 25 cm and the average width is 20 cm.

Stems:

*Color*.—Young wood: Yellow-Green Group 144B. Older wood: Yellow-Green Group 144A.

*Internodal distance*.—20 to 35 mm.

*Length of stems*.—On average, 15 cm from base of the stem to the flowering portion. 3 to 4 mm diameter.

*Surface texture*.—Young wood: Smooth. Older wood: Smooth.

Prickles:

*Incidence*.—3 to 4 mm per 10 cm of stem.

*Size*.—Average length: 6 mm.

*Color*.—Juvenile prickles are Greyed-Red Group 180C. Mature prickles are Greyed-Red Group 180C.

*Shape*.—Linear.

Plant foliage: On average, 5 leaflets.

*Compound leaf size*.—95 mm (l)×80 mm (w) on average.

*Quantity*.—3 leaves per 10 cm of stem.

*Color*.—Juvenile foliage: Upper Leaf Surface: Yellow-Green Group 147A to 146A. Greyed-Purple Group N186C at the margins. Lower Leaf Surface: Yellow-Green Group 147C. Mature foliage: Upper Leaf Surface: Yellow-Green Group 147A. Lower Leaf Surface: Yellow-Green Group 147C.

Plant leaves and leaflets:

*Stipules*.—Size: 11 mm in length. Shape: Linear, slightly broad based with outward extending apecies. Margins: Finely serrated. Color: Green Group 143A.

*Petiole*.—Length: 15 mm. 1 to 2 mm wide. Color: Upper surface is Yellow-Green Group 147C with anthocyanin: the color of Greyed-Purple Group 187A. Lower surface is Yellow-Green Group 144A.

*Rachis*.—Length: 25 mm on average. Color: Upper surface is Yellow-Green Group 147C with anthocyanin: the color of Greyed-Purple Group 187A. Lower surface is Yellow-Green Group 144A.

*Leaflet*.—Size: 55 mm in length by 35 mm wide. Margin: Serrate. General Shape: Elliptical. Apex Shape: Acute. Base Shape: Round. Texture: Smooth. Arrangement: Odd pinnate. Venation: Reticulate. Leaf Gloss: Moderately glossy.

Disease resistance: Above average resistance to powdery and downy mildew, black spot, and Botrytis under normal growing conditions.

Cold hardiness: The variety is tolerant to USDA Cold Hardiness Zone 6.

Heat tolerance: The variety has been found to be suitable for climate conditions found in the American Horticultural Society heat zone 7.

The invention claimed is:

1. A new and distinct variety of rose plant of the miniature class named 'Poulpah051', substantially as illustrated and described herein, due to its abundant, white flowers, vigorous growth, compact habit, suitability for production from softwood cuttings in pots, and durable flowers and foliage that make the variety suitable for distribution in the floral industry.

* * * * *

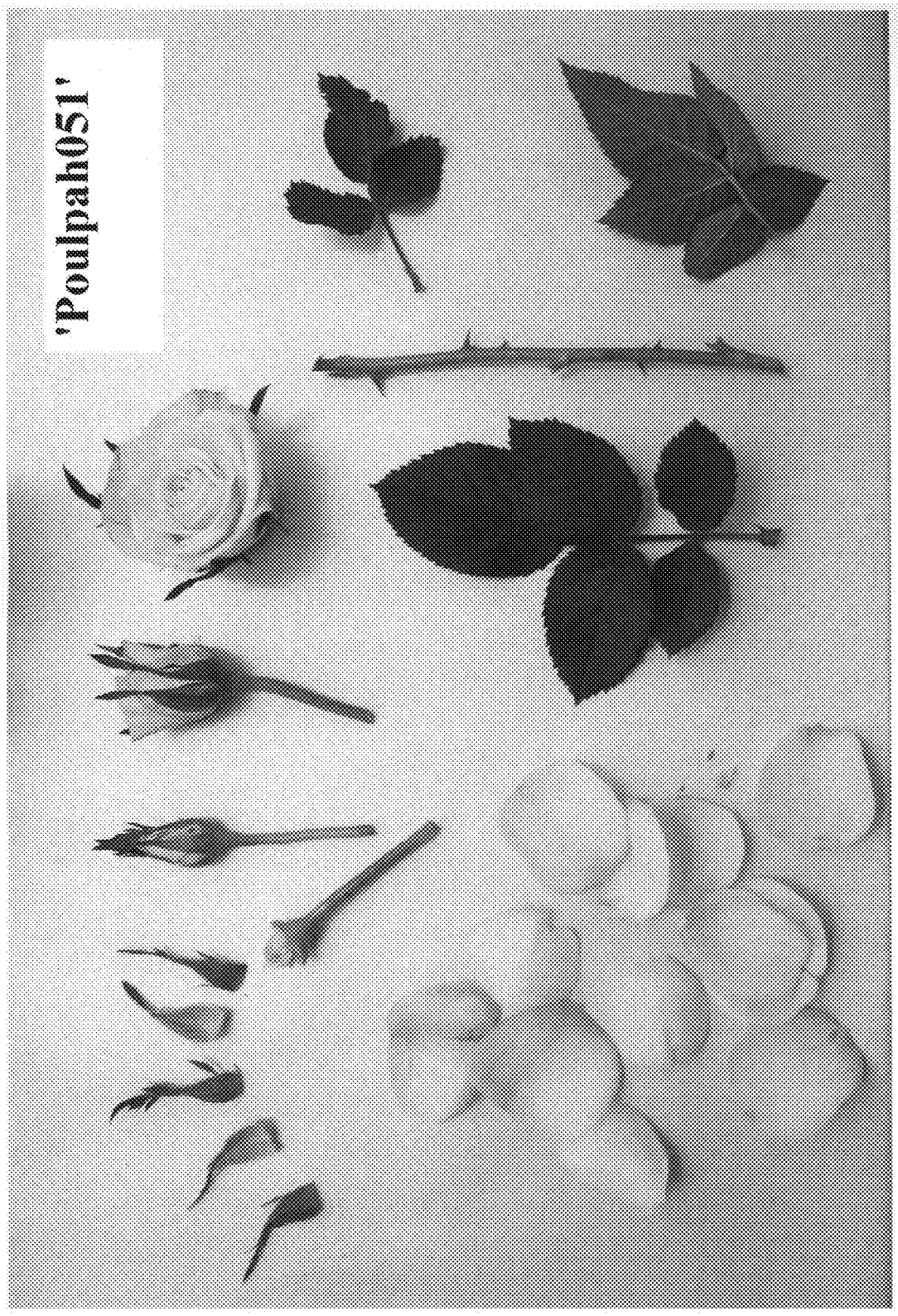
'Poulpah051'